United States Patent
Koyama

(10) Patent No.: US 10,398,322 B2
(45) Date of Patent: Sep. 3, 2019

(54) BIOLOGICAL INFORMATION MEASURING APPARATUS AND BLOOD PRESSURE ANALYZING METHOD

(71) Applicant: NIHON KOHDEN CORPORATION, Tokyo (JP)

(72) Inventor: Yukio Koyama, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 387 days.

(21) Appl. No.: 14/728,005

(22) Filed: Jun. 2, 2015

(65) Prior Publication Data
US 2015/0359444 A1    Dec. 17, 2015

(30) Foreign Application Priority Data

Jun. 11, 2014  (JP) .................................. 2014-120503

(51) Int. Cl.
*A61B 5/021*  (2006.01)
*A61B 5/04*   (2006.01)
(Continued)

(52) U.S. Cl.
CPC ...... *A61B 5/02108* (2013.01); *A61B 5/02116* (2013.01); *A61B 5/04012* (2013.01);
(Continued)

(58) Field of Classification Search
USPC ....................................................... 600/485
See application file for complete search history.

(56) References Cited

U.S. PATENT DOCUMENTS 5,392,780 A *  2/1995  Ogino .................. A61B 5/021
                                                    600/483
6,331,162 B1  12/2001  Mitchell
(Continued)

FOREIGN PATENT DOCUMENTS

JP    2-185231 A    7/1990
JP    10137202 A    5/1998
(Continued)

OTHER PUBLICATIONS

El-Ghazzawi, Z., et al. "An algorithm to extract blood-pressure waveform features during intra-aortic balloon pump assist." Engineering in Medicine and Biology Society, 1989. Images of the Twenty-First Century., Proceedings of the Annual International Conference of the IEEE Engineering in. IEEE, 1989.*
(Continued)

*Primary Examiner* — Christian Jang
*Assistant Examiner* — Mitchell E Alter
(74) *Attorney, Agent, or Firm* — Sughrue Mion, PLLC

(57) ABSTRACT

A biological information measuring apparatus includes a blood pressure pulse wave measuring unit configured to measure a blood pressure pulse wave of a subject, a unit pulse wave producing unit configured to produce unit pulse waves of a certain unit from the blood pressure pulse wave based on an analysis of heart beats of the subject, a unit pulse wave extracting unit configured to analyze the unit pulse waves produced by the unit pulse wave producing unit and to extract only necessary unit pulse waves in accordance with the analysis, and an output unit configured to perform an output based on the unit pulse waves extracted by the unit pulse wave extracting unit.

9 Claims, 8 Drawing Sheets

(51) Int. Cl.
*A61B 5/0456* (2006.01)
*A61B 5/00* (2006.01)
*A61B 5/0215* (2006.01)

(52) U.S. Cl.
CPC ............ *A61B 5/0456* (2013.01); *A61B 5/742* (2013.01); *A61B 5/0215* (2013.01)

(56) References Cited

U.S. PATENT DOCUMENTS

| | | |
|---|---|---|
| 2003/0158488 A1 | 8/2003 | Narimatsu et al. |
| 2005/0261597 A1* | 11/2005 | Kolluri ............... A61B 5/02225 600/513 |
| 2008/0255466 A1 | 10/2008 | Wellnhofer |
| 2010/0210954 A1* | 8/2010 | Bennett ................ A61B 5/0215 600/485 |
| 2010/0222650 A1 | 9/2010 | Tanishima et al. |
| 2011/0144918 A1 | 6/2011 | Inoue |
| 2012/0078123 A1 | 3/2012 | Futatsuyama et al. |
| 2012/0095353 A1 | 4/2012 | Mori et al. |
| 2012/0215275 A1 | 8/2012 | Wenzel et al. |

FOREIGN PATENT DOCUMENTS

| | | |
|---|---|---|
| JP | 10314127 A | 12/1998 |
| JP | 2003235818 A | 8/2003 |
| JP | 2007523704 A | 8/2007 |
| JP | 2008061824 A | 3/2008 |
| JP | 2008-79813 A | 4/2008 |
| JP | 2010088576 A | 4/2010 |
| JP | 2010-200901 A | 9/2010 |
| JP | 2011-92556 A | 5/2011 |
| JP | 2012-71018 A | 4/2012 |
| JP | 2012161556 A | 8/2012 |

OTHER PUBLICATIONS

Zong, W., G. B. Moody, and R. G. Mark. "Reduction of false arterial blood pressure alarms using signal quality assessement and relationships between the electrocardiogram and arterial blood pressure." Medical and Biological Engineering and Computing 42.5 (2004): 698-706.*

Li, et al. "Development of software of the pulse wave data analysis and management system" 2012 IEEE Symposium on Electrical & Electronics Engineering.*

European Search Report dated Oct. 22, 2015 by the European Patent Office in counterpart European Application No. 15170469.9.

Zong W et al: "Reduction of false arterial blood pressure alarms using signal quality assessment and relationships between the electrocardiogram and arterial blood pressure", Medical & Biological Engineering & Computing, Springer, Berlin, DE, vol. 42, No. 5, Sep. 1, 2004 (Sep. 1, 2004), pp. 698-706, XP019834498.

Lidierth et al: "sigTOOL: A MATLAB-based environment for sharing laboratory-developed software to analyze biological signals", Journal of Neuroscience Methods, Elsevier Science Publisher B.V., Amsterdam, NL, vol. 178, No. 1, Mar. 30, 2009 (Mar. 30, 2009), pp. 188-196, XP025912856.

Office Action dated Feb. 28, 2017 issued by the Japanese Patent Office in counterpart Japanese Patent Application No. 2014-120503.

Communication dated Jun. 29, 2018, issued by the Japanese Patent Office in counterpart Japanese Application No. 2017-182741.

* cited by examiner

BIOLOGICAL INFORMATION MEASURING APPARATUS AND BLOOD PRESSURE ANALYZING METHOD

CROSS-REFERENCE TO RELATED APPLICATION(S)

The present application claims priority from Japanese Patent Application No. 2014-120503 filed on Jun. 11, 2014, the entire content of which is incorporated herein by reference.

BACKGROUND

The presently disclosed subject matter relates to a biological information measuring apparatus and a blood pressure analyzing method, and program which invasively measure the blood pressure of the subject.

In patient monitoring, the blood pressure is regarded as an important index. For a severe patient, particularly, it is usual to invasively monitor the arterial and venous pressures. In the invasive blood pressure measurement, a catheter or the like is placed in a vessel or the heart, and a blood pressure waveform or a blood pressure value is continuously measured.

The heart exists in the chest cavity, and hence an invasive blood pressure waveform is affected by variation of the intrapleural pressure due to the respiration of the patient, thereby causing a problem in that the blood pressure waveform and the blood pressure value are not correctly obtained. For example, the central venous pressure (CVP) in the vicinity of the right atrial is low, and hence markedly affected by the respiratory variation. Moreover, parameters of the low-pressure system may be affected not only by the respiratory variation, but also by body motion or the like.

According to a related art, to suppress such influences of respiratory variation and the like on an invasive blood pressure waveform, an averaging process is performed on obtained values of the blood pressure.

According to another related art disclosed in JP2010-200901A, a biological signal measuring apparatus is configured to calculate blood pressure in synchronization with a respiratory waveform obtained by a respiratory sensor.

However, the averaging process has a problem in that, in a case in which a large influence is exerted by respiratory variation or the like, sufficient effect cannot be obtained. The related art disclosed in JP2010-200901A requires a respiratory waveform sensor in addition to equipments for measuring the blood pressure.

SUMMARY

Illustrative aspects of the present invention provide a biological information measuring apparatus and a blood pressure analyzing method that, without complicating a configuration, can obtain a blood pressure condition in which effect of respiratory variation, body motion or the like is suppressed.

According to an illustrative aspect of the present invention, a biological information measuring apparatus includes a blood pressure pulse wave measuring unit configured to measure a blood pressure pulse wave of a subject, a unit pulse wave producing unit configured to produce unit pulse waves of a certain unit from the blood pressure pulse wave based on an analysis of heart beats of the subject, a unit pulse wave extracting unit configured to analyze the unit pulse waves produced by the unit pulse wave producing unit and to extract only necessary unit pulse waves in accordance with the analysis, and an output unit configured to perform an output based on the unit pulse waves extracted by the unit pulse wave extracting unit.

According to another illustrative aspect of the present invention, a blood pressure analyzing method includes measuring a blood pressure pulse wave of a subject, producing unit pulse waves of a certain unit from the blood pressure pulse wave based on an analysis of heart beats of the subject, analyzing the produced unit pulse waves and extracting only necessary unit pulse waves in accordance with the analysis, and performing an output based on the extracted unit pulse waves.

According to another illustrative aspect of the present invention, a non-transitory computer readable medium stores a program that, when executed by a computer, causes the computer to execute a method including producing unit pulse waves of a certain unit from a blood pressure pulse wave of a subject, analyzing the produced unit pulse waves and extracting only necessary unit pulse waves in accordance with the analysis, and performing an output based on the extracted unit pulse waves.

According to another illustrative aspect of the present invention, a program causes a computer to execute a method including producing unit pulse waves of a certain unit from a blood pressure pulse wave of a subject, analyzing the produced unit pulse waves and extracting only necessary unit pulse waves in accordance with the analysis, and performing an output based on the extracted unit pulse waves.

DETAILED DESCRIPTION

Figure 1:
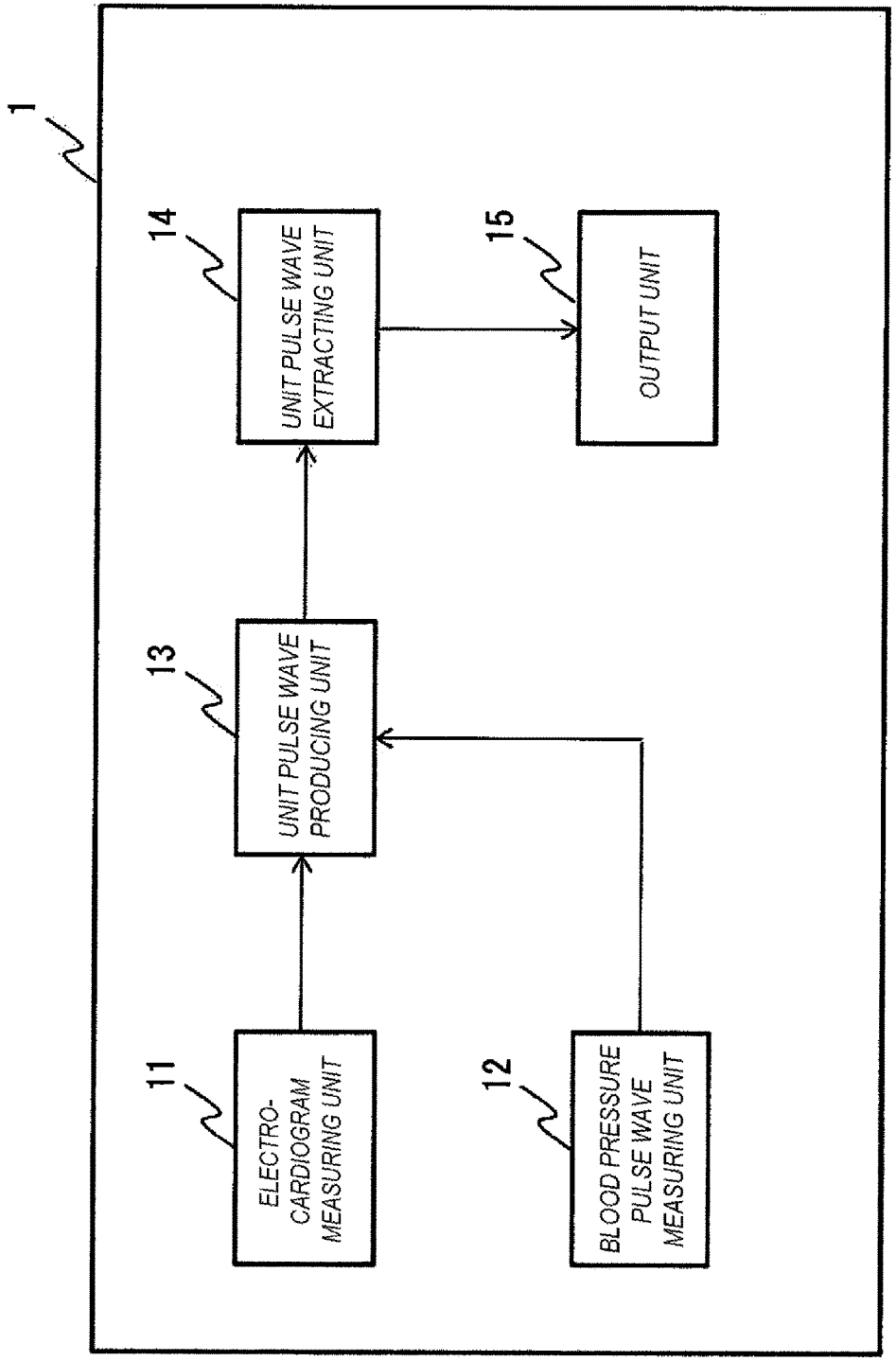
FIG. 1 is a block diagram illustrating a configuration of a biological information measuring apparatus according to an exemplary embodiment of the present invention.

Hereinafter, exemplary embodiments of the present invention will be described with reference to the drawings. FIG. 1 is a block diagram illustrating a configuration of a biological information measuring apparatus 1 according to an exemplary embodiment of the present invention. The biological information measuring apparatus 1 includes an electrocardiogram measuring unit 11, a blood pressure pulse wave measuring unit 12, a unit pulse wave producing unit 13, a unit pulse wave extracting unit 14, and an output unit 15. The biological information measuring apparatus 1 is configured as, for example, an invasive manometer. The biological information measuring apparatus 1 may be configured to have one or more functions in addition to invasive measurement of the blood pressure.

The electrocardiogram measuring unit 11 includes, for example, electrocardiogram electrodes and an amplifying circuit. The electrocardiogram electrodes are attached to the chest and the like of the subject. The electrocardiogram measuring unit 11 acquires an electrocardiogram (ECG) based on electrocardiogram signals obtained from the electrocardiogram electrodes, and supplies the acquired electrocardiogram (ECG) to the unit pulse wave producing unit 13.

The blood pressure pulse wave measuring unit 12 is configured to invasively measure a blood pressure pulse wave of a subject. The blood pressure pulse wave measuring unit 12 includes, for example, a blood pressure transducer, an amplifying circuit, a catheter, various tubes, a three-way cock, etc. The blood pressure pulse wave to be measured by the blood pressure pulse wave measuring unit 12 may be a pulse wave of any blood vessel. In the following description, the blood pressure pulse wave to be measured relates to a central venous (CV). The user such as a doctor adjusts the zero point of the blood pressure value before start of the measurement of the blood pressure. The blood pressure transducer is opened to the atmosphere, and then the pressure applied to the blood pressure transducer is made zero. In the blood pressure pulse wave measuring unit 12, the blood pressure is converted to a blood pressure signal by the blood pressure transducer, and the blood pressure signal is supplied to the unit pulse wave producing unit 13. The process of measuring the blood pressure pulse wave may be performed by the blood pressure pulse wave measuring unit 12, in a similar manner as a general invasive blood pressure measurement process (see, e.g., Sakurai and Watanabe, "ME Hayawakari Q&A 3—Ketsuatsukei, Shinpakushutsuryokei, Ketsuryukei", NANKODO, pp. 33-92).

Figure 2:
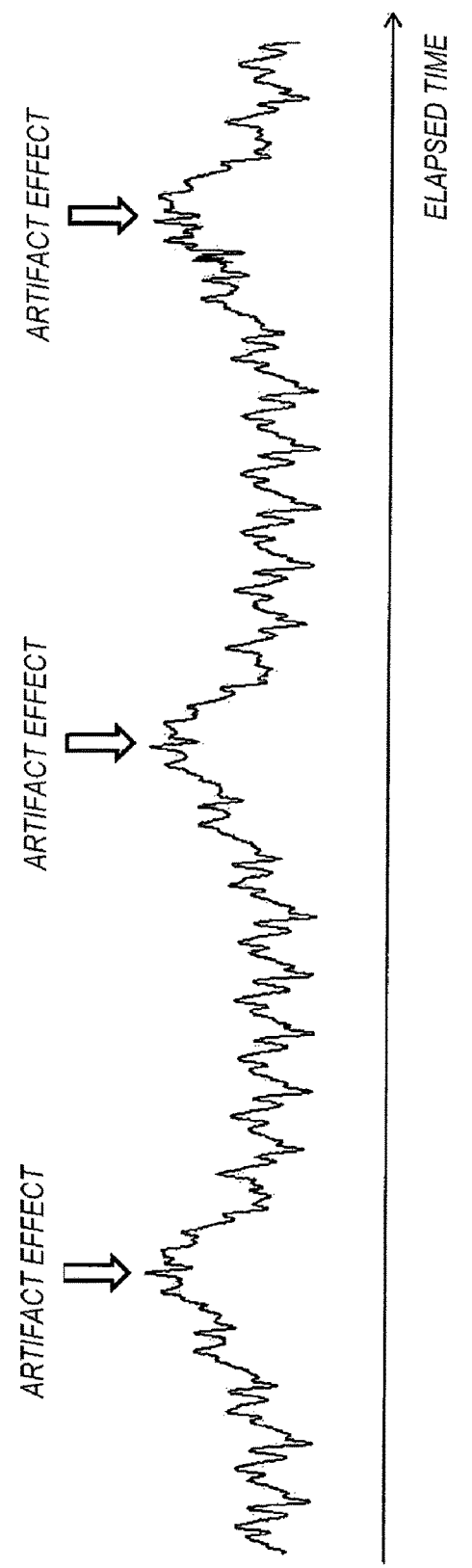
FIG. 2 is a chart showing an example of a blood pressure waveform of a central venous (CV)

The blood pressure pulse wave of the central venous (CV) which is measured by the blood pressure pulse wave measuring unit 12 will be described with reference to FIG. 2. FIG. 2 shows an example of the blood pressure pulse wave of the central venous (CV). The central venous pressure (CVP) is easily influenced by respiratory variation, body motion, and the like. FIG. 2 shows such waveforms affected by a respiration-originated artifact.

Referring again to FIG. 1, the unit pulse wave producing unit 13 produces a plurality of unit pulse waves from the blood pressure pulse wave, based on the electrocardiogram measured by the electrocardiogram measuring unit 11. A unit pulse wave is produced from the blood pressure pulse wave based on the heart beats, and configured by the pulse wave of the central venous of a certain unit (preferably, per cardiac cycle). Specifically, the unit pulse wave producing unit 13 detects QRS waves from the electrocardiogram, obtains one cardiac cycle from the detected timings of the QRS waves, and produces a plurality of unit pulse waves from the blood pressure pulse wave by using the one cardiac cycle. Hereinafter, a specific example of the production process by the unit pulse wave producing unit 13 will be described with reference to FIG. 3.

Figure 3:
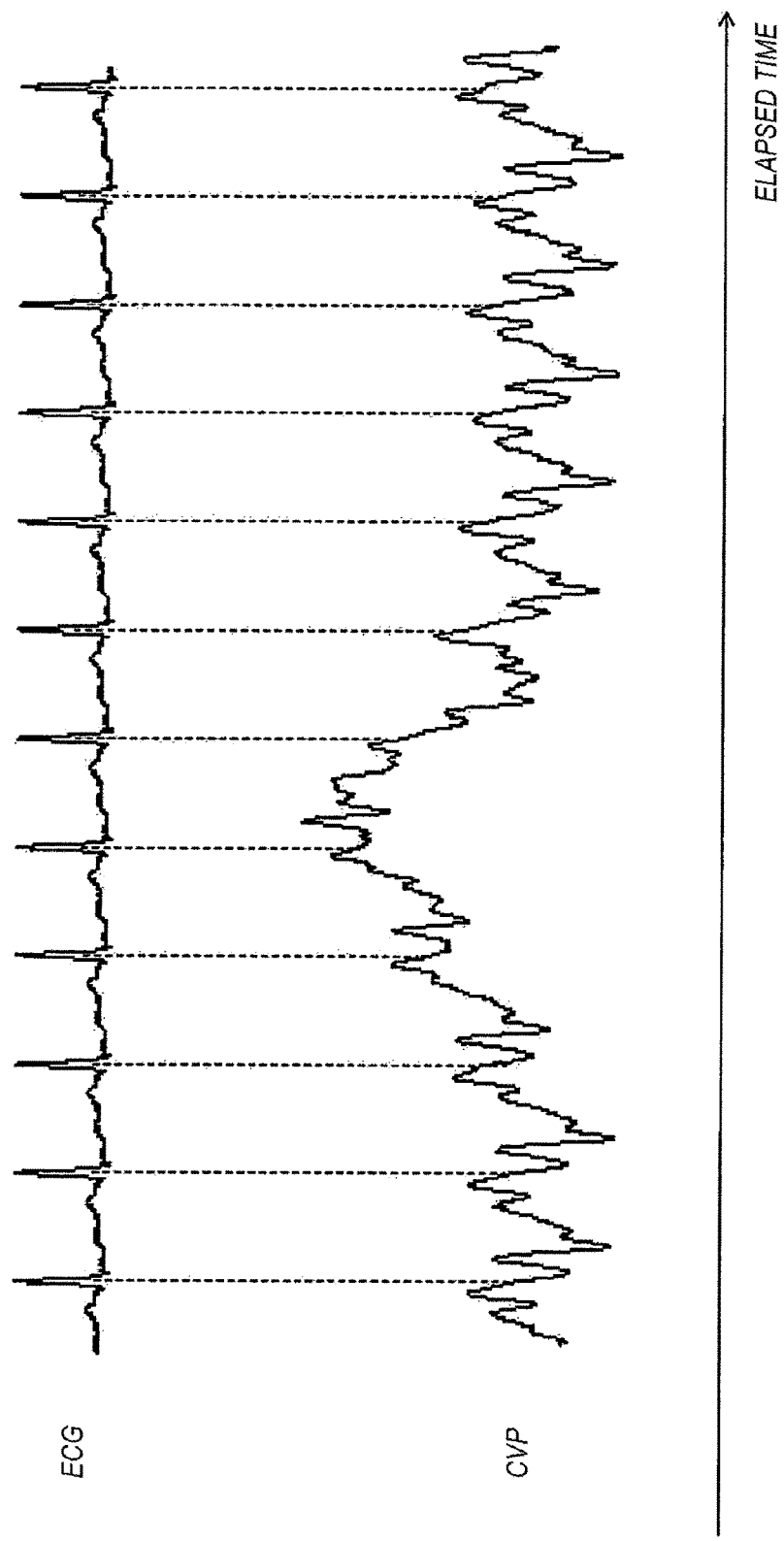
FIG. 3 is a chart showing examples of an electrocardiogram measured by an electrocardiogram measuring unit and a blood pressure waveform measured by a blood pressure pulse wave measuring unit.

FIG. 3 is a view showing the electrocardiogram measured by the electrocardiogram measuring unit 11, and the blood pressure pulse wave measured by the blood pressure pulse wave measuring unit 12. The unit pulse wave producing unit 13 analyzes the electrocardiogram, and detects QRS waves. The so-called RR interval can be deemed to be equivalent to the heart beat interval. Therefore, the unit pulse wave producing unit 13 produces a plurality of unit pulse waves from the blood pressure pulse wave by using the RR interval. In the case where the blood pressure pulse wave is divided by time intervals equal to the RR interval, each unit pulse wave coincides with the blood pressure pulse wave of a time period corresponding to the one cardiac cycle. The above-described detection of the QRS waves by the unit pulse wave producing unit 13 is performed for knowing the time intervals of the cardiac beats. Although the accuracy is low, therefore, the unit pulse wave producing unit 13 may produce unit pulse waves by using detection of the T waves. The unit pulse wave producing unit 13 may produce unit pulse waves corresponding to a plurality of heart beats (for example, per two cardiac cycles). When unit pulse waves are produced in the unit of one cardiac cycle, however, precise analysis can be performed by, for example, the unit pulse wave extracting unit 14 which will be described later.

Figure 4:
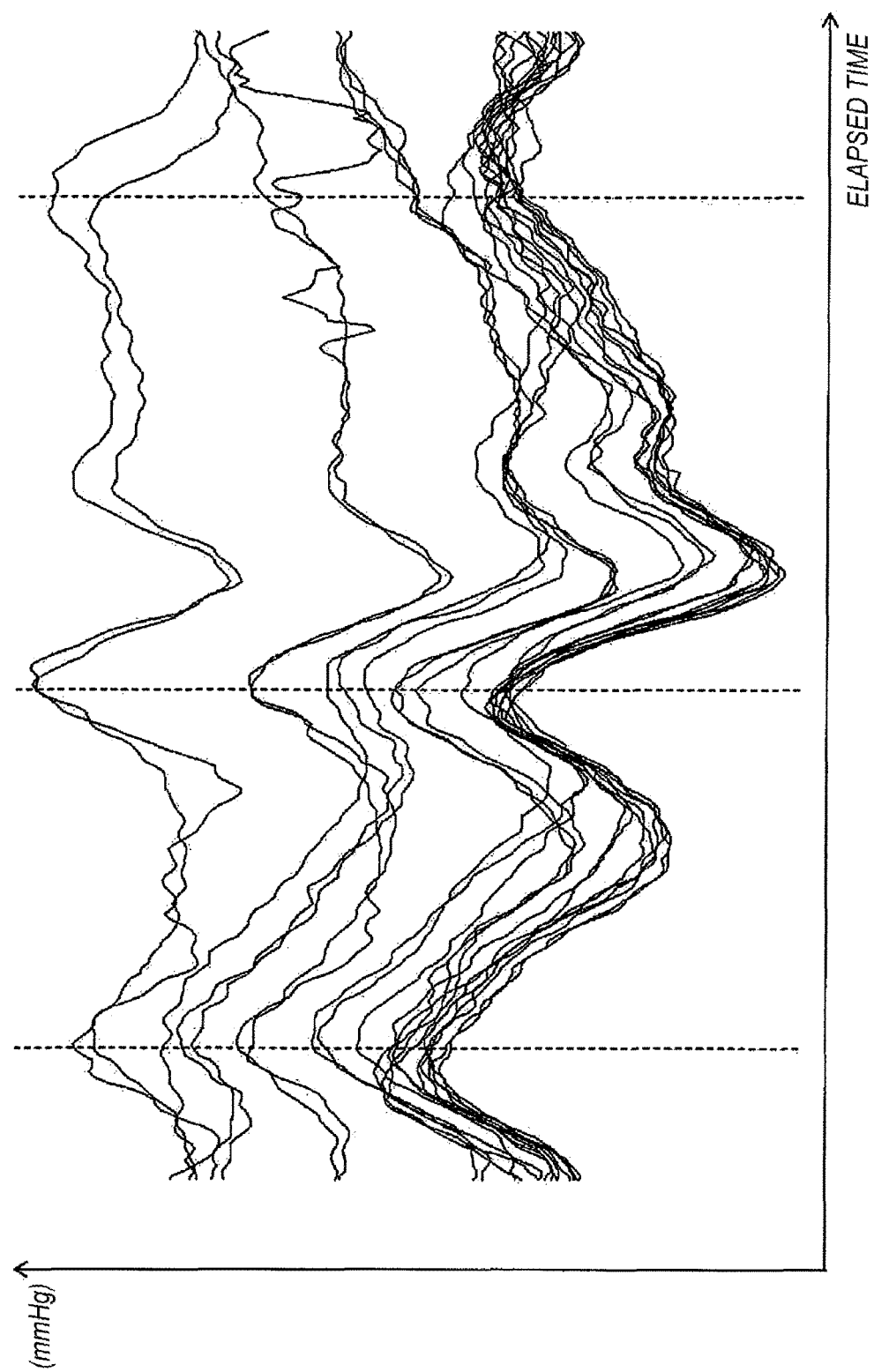
FIG. 4 is a graph showing examples of unit pulse waves produced by a unit pulse wave producing unit in a superposed manner.

FIG. 4 is a graph showing produced unit pulse waves, in a superposed manner. The example of FIG. 4 shows that the average blood pressure values of the unit pulse waves, and the waveforms of the pulse waves are shifted because of influences of respiratory variation and the like. Specifically, it is seen that the pulse pressure values of a small number of unit pulse waves are raised in whole.

Referring again to FIG. 1, the unit pulse wave producing unit 13 supplies the plurality of unit pulse waves which are calculated by the above-described production process, to the unit pulse wave extracting unit 14. The unit pulse wave extracting unit 14 analyzes the unit pulse waves, and extracts only necessary unit pulse waves in accordance with the analysis. Hereinafter, the process of analyzing and extracting the unit pulse waves will be described in detail.

Figure 5:
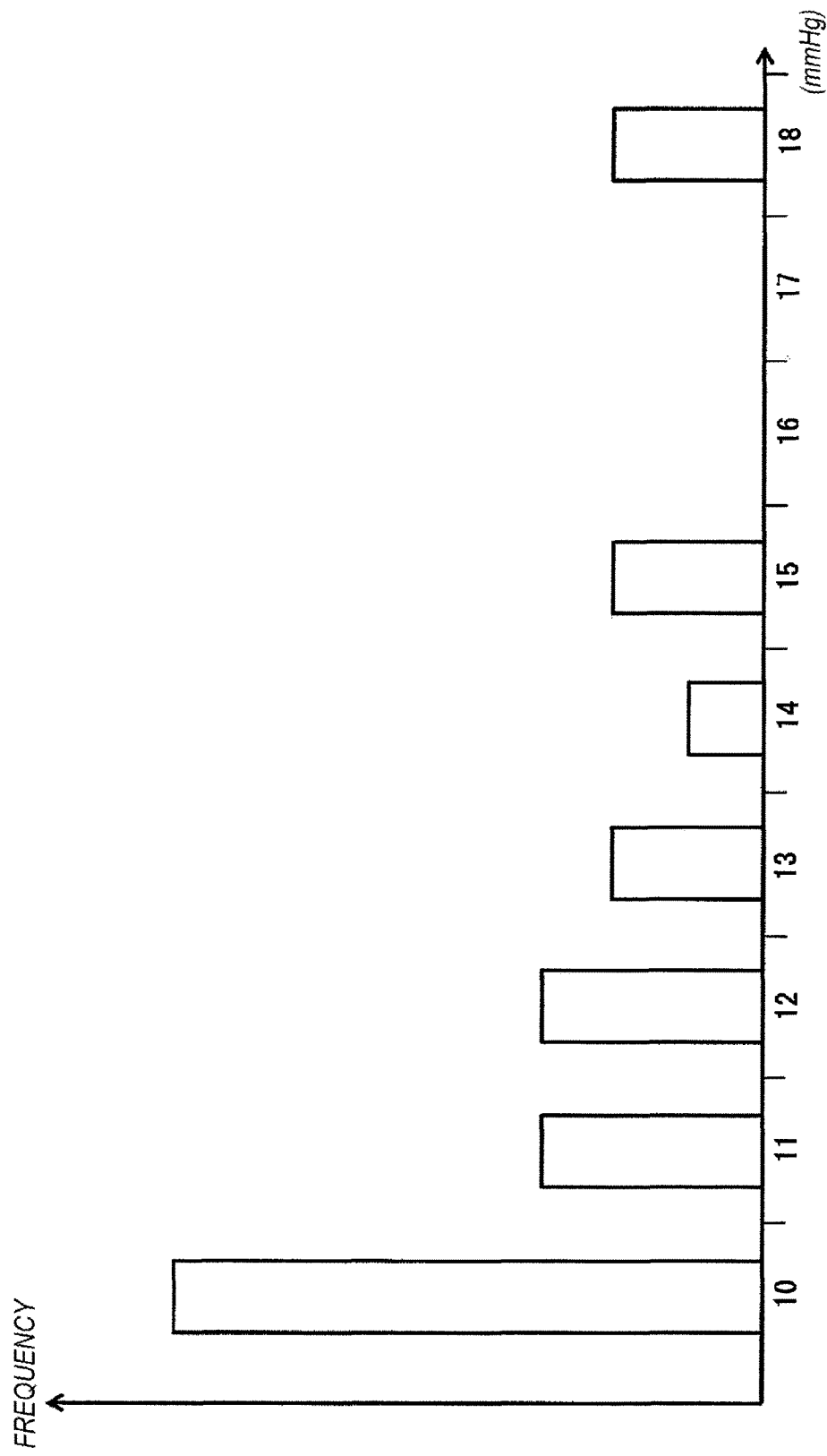
FIG. 5 is an example of a histogram produced by a unit pulse wave extracting unit.

The unit pulse wave extracting unit 14 statistically analyzes the data of the unit pulse waves produced by the unit pulse wave producing unit 13. For example, the unit pulse wave extracting unit 14 calculates the average blood pressure value of each of the unit pulse waves, and produces a histogram using the average blood pressure values. FIG. 5 shows an example of the histogram which is produced by the unit pulse wave extracting unit 14 based on the data of the unit pulse waves shown in FIG. 4.

Figure 6:
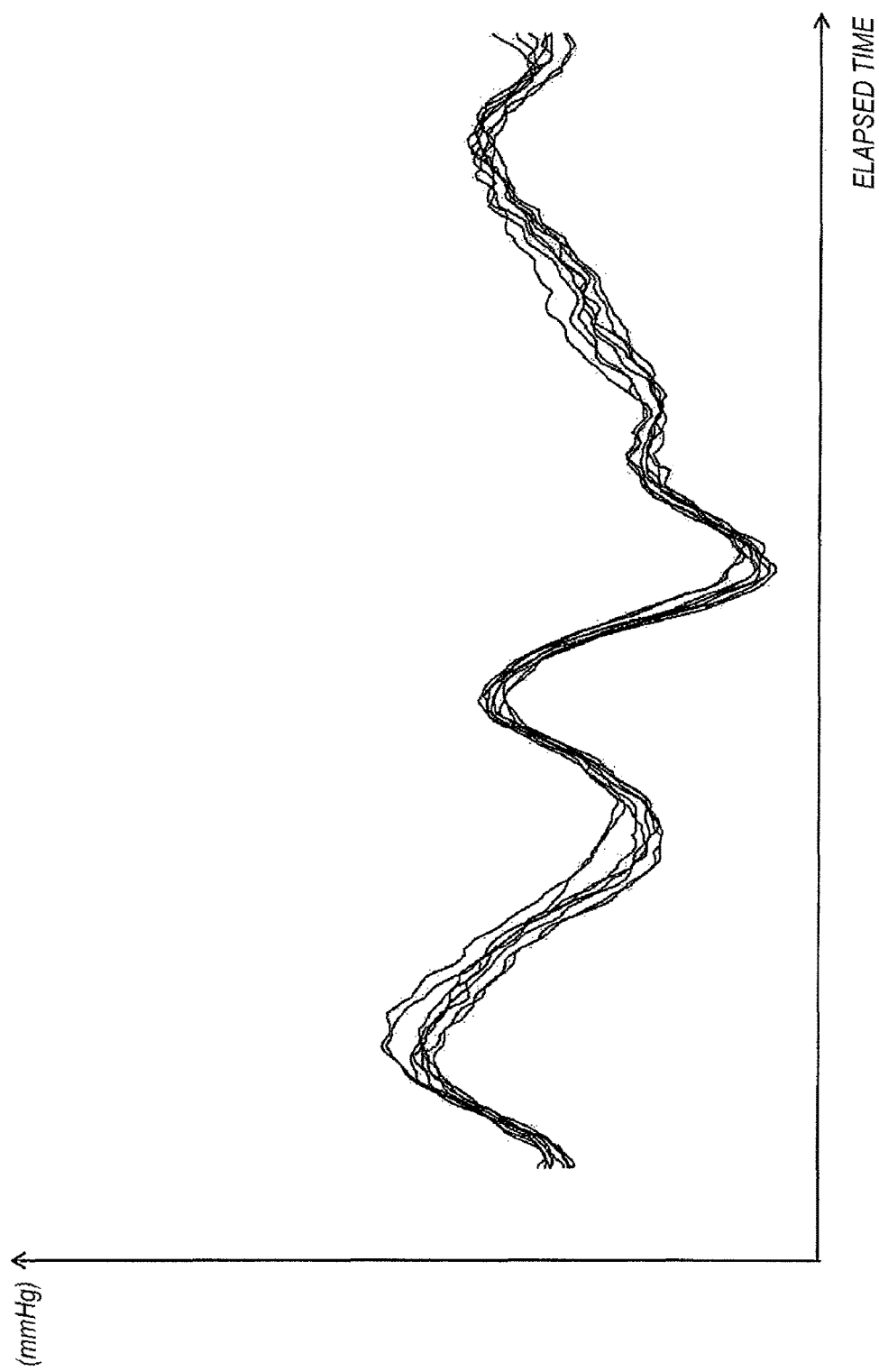
FIG. 6 is a graph showing only unit pulse waves of a class including a mode value of an average blood pressure value.

The histogram shown in FIG. 5 is produced by using the average blood pressure values of the unit pulse waves (for example, calculated by rounding to the nearest whole number). Alternatively, the histogram may be produced by using the minimum or maximum blood pressure value of each of the unit pulse waves. In the example of FIG. 5, the mode value is 10 mmHg. The unit pulse wave extracting unit 14 extracts only unit pulse waves in which the average blood pressure value belongs to the mode value (or belongs to the vicinity of the mode value). FIG. 6 is a view showing an example in which only unit pulse waves of the class including the mode value of the average blood pressure values are extracted from the unit pulse waves shown in FIG. 4. It is possible to regard a unit pulse wave of the mode value as that which is stable, and which is not affected by an artifact such as respiratory variation.

Although, in the above-described example, the unit pulse wave extracting unit 14 extracts unit pulse waves by using the mode value, the extraction method is not limited to this. The extraction process of the unit pulse wave extracting unit 14 is intended to extrude abnormal unit pulse waves which are affected by respiratory variation and the like, and extract only necessary unit pulse waves. Therefore, the unit pulse wave extracting unit 14 may extract necessary unit pulse waves by using the average value or the median value in place of the mode value. Namely, it is requested that the unit pulse wave extracting unit 14 be configured so as to perform a statistical analysis based on the data of the unit pulse waves produced by the unit pulse wave producing unit 13, and extract only necessary unit pulse waves by using statistical values obtained in the statistical analysis. It is supposed that, in the case where influences of respiratory variation exist, parameters of the low-pressure system such as the central venous wave are high when an artificial respirator is used, and low in the case of spontaneous respiration. Therefore, the unit pulse wave extracting unit 14 preferably performs the process by using the mode value in place of the average value or the median value.

The unit pulse wave extracting unit 14 supplies the extracted unit pulse waves to the output unit 15. Here, the unit pulse wave extracting unit 14 may supply only the extracted unit pulse waves to the output unit 15, or perform a discriminating operation such as addition of a flag to unit pulse waves which are extraction targets, and then supply all unit pulse waves to the output unit 15.

The output unit 15 performs an output based on the unit pulse waves extracted by the unit pulse wave extracting unit 14. Hereinafter, an example of the output process performed by the output unit 15 will be described.

A first output example will be described. The output unit 15 displays the average blood pressure values and the like of the extracted unit pulse waves, on a display monitor disposed in the biological information measuring apparatus 1. The output unit 15 performs a statistical processing (e.g., averaging in this example) to the extracted unit pulse waves to calculate the average blood pressure values (e.g., 10.4 mmHg), and displays the calculated average blood pressure values on the display monitor. Alternatively, the output unit 15 may display the calculated average blood pressure values on the display monitor, and store the values on a hard disk or the like incorporated in the biological information measuring apparatus 1.

Then, a second output example will be described with reference to FIG. 7. The output unit 15 displays only the extracted unit pulse waves on the display monitor. The output unit 15 performs averaging by using the extracted unit pulse waves to calculate an average pulse wave, and displays also the calculated pulse wave on the display monitor. In the example shown in FIG. 7, the average pulse wave which is calculated from the extracted average unit pulse waves is indicated by thick circles. It is a matter of course that the output unit 15 can display the average pulse wave which is obtained by averaging, in the form of a continuous waveform. When referring to FIG. 7, the user (doctor or nurse) can visually know outlines of the pulse waveform and pulse pressure value of the central venous which are seemed not to be affected by respiratory variation and the like.

Next, a third output example will be described with reference to FIG. 8. The output unit 15 displays the extracted unit pulse waves, and the unit pulse waves which are not extraction targets, with different display effects. In the example shown in FIG. 8, the unit pulse waves which are extraction targets are indicated by solid lines, and those which are not extraction targets are indicated by broken lines. When referring to FIG. 8, the user (doctor or nurse) can visually know outlines of the pulse waveform and pulse pressure value of the central venous which are seemed not to be affected by respiratory variation and the like. Moreover, the user (doctor or nurse) can visually know the degree of the influence of respiratory variation and the like (number (rate) of pulse waves which are affected by respiratory variation and the like, and the degrees of changes of pulse waves caused by respiratory variation and the like).

Then, effects of the biological information measuring apparatus 1 of the embodiment will be described. The unit pulse wave producing unit 13 produces a plurality of unit pulse waves from the blood pressure pulse wave. Then, the unit pulse wave extracting unit 14 analyzes the unit pulse waves, and extracts only necessary unit pulse waves. In the extraction, unit pulse waves which are affected by respiratory variation and the like are not set as extraction targets. The output unit 15 outputs the extracted unit pulse waves in the form which is recognizable by the user, thereby enabling the user to know the correct condition (blood pressure waveform, blood pressure value, and the like) of the blood pressure pulse wave.

In the above-described technique, the biological information measuring apparatus 1 extracts only unit pulse waves which are supposed not to be affected by respiratory variation and the like, without measuring a parameter relating to respiration. Namely, the biological information measuring apparatus 1 can calculate the blood pressure condition (blood pressure waveform, blood pressure value, and the like) in which influences of respiratory variation and the like are suppressed, without using a respiratory sensor or the like. In the technique using a respiratory sensor, it is difficult to consider influences of body motion and the like. By contrast, the unit pulse wave producing unit 13 is configured so as to eliminate an abnormal value irrespective of a cause of an artifact, and therefore can correctly extract unit pulse waves.

Preferably, the unit pulse wave producing unit 13 detects QRS waves from the electrocardiogram, and produces unit pulse waves in the unit of one beat from the blood pressure pulse wave by using the RR interval. When analysis by using unit pulse waves of each beats is performed, it is possible to analyze the blood pressure pulse waves corresponding to the heart beats. In an electrocardiogram, QRS waves are peaks in which the voltage value is sharply changed. Therefore, the use of QRS waves enables the unit pulse wave producing unit 13 to accurately produce unit pulse waves.

The unit pulse wave extracting unit 14 is configured to perform a statistical processing on the produced unit pulse waves, and to extracts only necessary unit pulse waves by using statistical values (preferably, the mode value). The statistical processing here is, for example, a general statistical processing, and the calculation amount is not large. Therefore, the unit pulse wave extracting unit 14 can accurately extract only necessary unit pulse waves by performing a simple calculation process.

The output unit 15 outputs (preferably, displays) the unit pulse waves extracted by the unit pulse wave extracting unit 14, in various forms. When the output unit 15 calculates and displays the average blood pressure values of the extracted unit pulse waves, for example, the user can obtain the correct average blood pressure values which are not affected by respiratory variation and the like.

Figure 7:
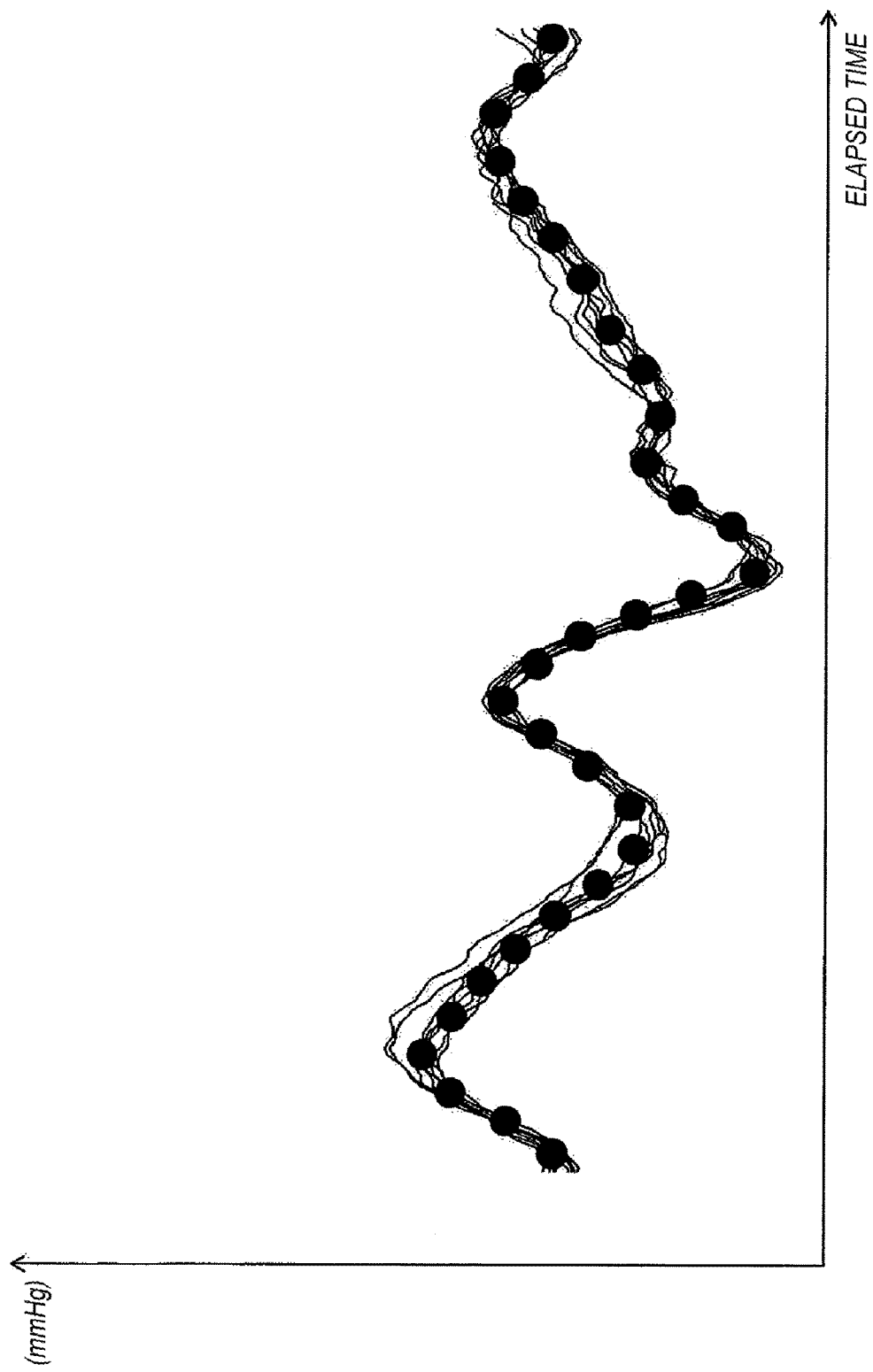
FIG. 7 is a chart illustrating an example of an output display of an output unit.

As shown in FIG. 7, the output unit 15 can display also unit pulse waves which are supposed not to be affected by respiratory variation and the like, on the display screen. When referring to the display (FIG. 7), the user (doctor or nurse) can visually know the pulse waveform and pulse pressure value of the central venous which are seemed not to be affected by respiratory variation and the like.

Figure 8:
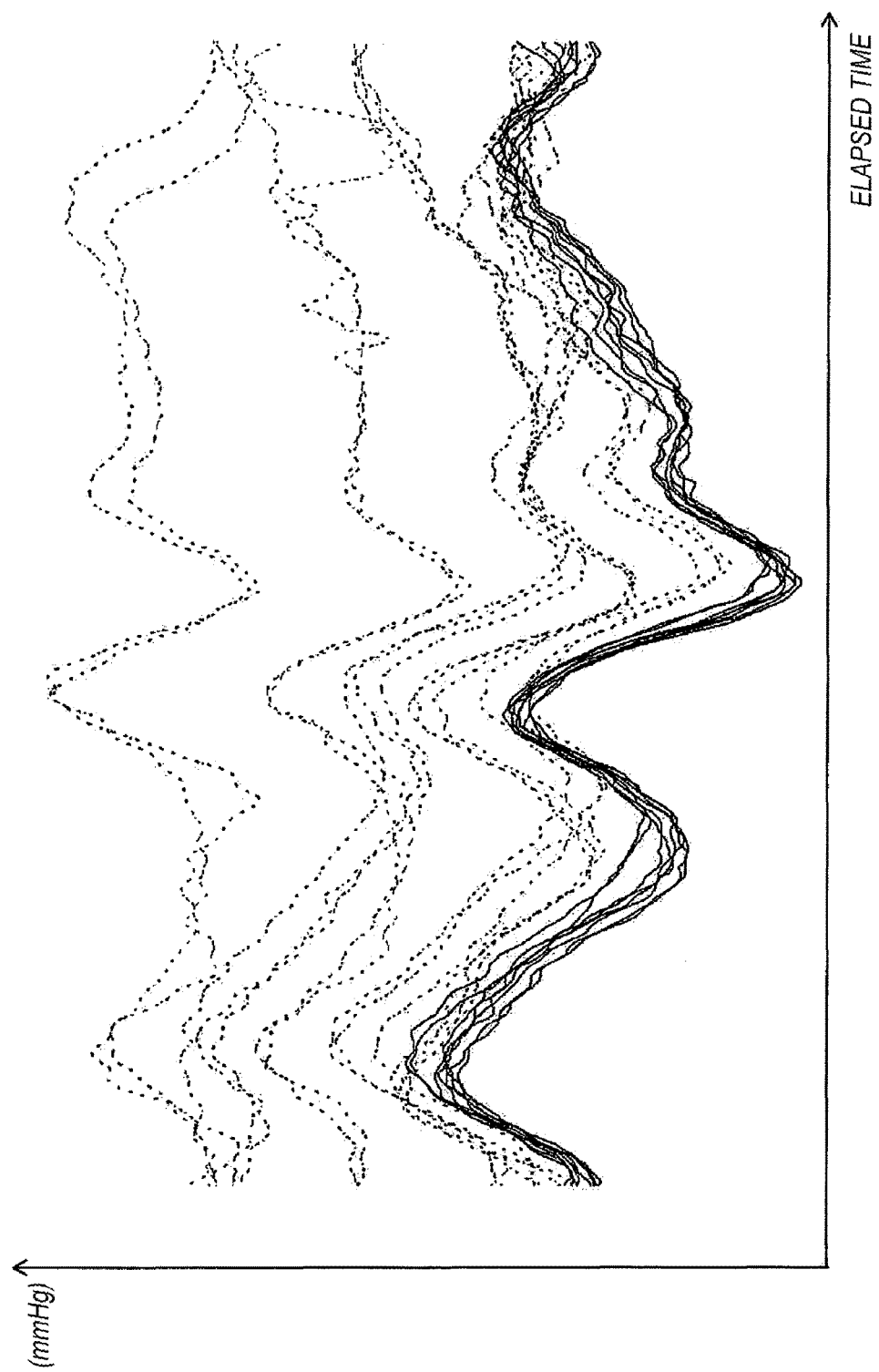
FIG. 8 is a chart illustrating another example of the output display of the output unit.

As shown in FIG. 8, moreover, the output unit 15 may display unit pulse waves which are supposed not to be affected by respiratory variation and the like, with a display effect (color, line type, and the like) that is different from that with which unit pulse waves that are supposed to be affected by respiratory variation and the like are displayed. When referring to the display (FIG. 8), the user (doctor or nurse) can visually know the degree of the influence of respiratory variation and the like (for example, the degree by which the pulse wave is changed by respiratory variation).

Although, in the above description, the unit pulse wave producing unit 13 produces unit pulse waves based on an electrocardiogram, the production process is not limited to this. For example, the biological information measuring apparatus 1 may have an arterial blood pressure measuring unit (not shown) in place of the electrocardiogram measuring unit 11. The arterial blood pressure measuring unit measures a change of the pressure of the arterial blood. The value of the arterial blood pressure is changed in accordance with the timing of the heat beat. The unit pulse wave producing unit 13 calculates the heart beat period in accordance with the change of the pressure value, and produces unit pulse waves from the blood pressure pulse wave by using the calculated heart beat period. The other processes are similar to those described above.

The unit pulse wave producing unit 13 may not use the information which is measured by the electrocardiogram measuring unit 11 (or the arterial blood pressure measuring unit), and may analyze the blood pressure pulse wave itself (in the above-described example, the pulse wave of the central venous) and, in accordance with the result of the analysis, produce a plurality of unit pulse waves from the blood pressure pulse wave. Referring to FIG. 4, approximately three maximal values (in the vicinities of the broken line axes in the figure) appear in many unit pulse waves corresponding to one heart beat. The unit pulse wave producing unit 13 detects the regularity, and estimates the time period between heart beats. Then, the unit pulse wave producing unit 13 may produce unit pulse waves from the blood pressure pulse wave by using the estimated time period between heart beats.

That is, the unit pulse wave producing unit 13 is configured to produce unit pulse waves from the blood pressure pulse wave using analysis of heart beats (e.g., analysis of electrocardiogram and heart beat period).

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

Exemplary embodiments of the present invention are very useful in analysis of not only a central venous but also any blood vessels (particularly, a blood vessel having a blood pressure value of a low-pressure system). For example, the blood pressure pulse wave measuring unit 12 may be configured to detect a blood pressure pulse wave of a pulmonary artery or the like.

The process of producing unit pulse waves in the unit pulse wave producing unit 13, extracting unit pulse waves in the unit pulse wave extracting unit 14, and the output process in the output unit 15 may be implemented as a computer program which operate in the biological information measuring apparatus 1. Namely, the biological information measuring apparatus 1 includes a configuration of a general computer, such as a central processing unit (CPU) and a memory device.

The program may be stored in a non-transitory computer readable medium of various types, and executed on a computer. The non-transitory computer readable medium includes tangible storage media of various types. Examples of the non-transitory computer readable medium include magnetic recording media (e.g., a flexible disk, a magnetic tape, and a hard disk drive), a CD-ROM (Read Only Memory), a CD-R, a CD-R/W, a semiconductor memory (e.g., a mask ROM, a programmable ROM (PROM), an erasable PROM (EPROM), a flash ROM, and a random access memory (RAM)). Alternatively, the program may be supplied to the computer by means of a transitory computer readable medium of various types. Examples of the transitory computer readable medium include an electrical signal, an optical signal, and an electromagnetic wave. The transitory computer readable medium can supply the programs to the computer through a wired communication path such as a metal wire or an optical fiber, or a wireless communication path.

According to exemplary embodiments of the present invention, a biological information measuring apparatus includes a blood pressure pulse wave measuring unit configured to measure a blood pressure pulse wave of a subject, a unit pulse wave producing unit configured to produce unit pulse waves of a certain unit from the blood pressure pulse wave based on an analysis of heart beats of the subject, a unit pulse wave extracting unit configured to analyze the unit pulse waves produced by the unit pulse wave producing unit and to extract only necessary unit pulse waves in accordance with the analysis, and an output unit configured to perform an output based on the unit pulse waves extracted by the unit pulse wave extracting unit.

According to exemplary embodiments of the present invention, a blood pressure analyzing method includes measuring a blood pressure pulse wave of a subject, producing unit pulse waves of a certain unit from the blood pressure pulse wave based on an analysis of heart beats of the subject, analyzing the produced unit pulse waves and extracting only necessary unit pulse waves in accordance with the analysis, and performing an output based on the extracted unit pulse waves.

According to exemplary embodiments of the present invention, a non-transitory computer readable medium stores a program that, when executed by a computer, causes the computer to execute a method including producing unit pulse waves of a certain unit from a blood pressure pulse wave of a subject, analyzing the produced unit pulse waves and extracting only necessary unit pulse waves in accordance with the analysis, and performing an output based on the extracted unit pulse waves.

According to exemplary embodiments the present invention, a program causes a computer to execute a method including producing unit pulse waves of a certain unit from a blood pressure pulse wave of a subject, analyzing the produced unit pulse waves and extracting only necessary unit pulse waves in accordance with the analysis, and performing an output based on the extracted unit pulse waves.

According exemplary embodiments of the present invention, the unit pulse waves are produced from the blood pressure pulse wave based on the heart beats of the subject. The unit pulse waves are analyzed, and only unit pulse waves, from which an abnormal value and the like are removed, are extracted. The extracted unit pulse waves are output in a form which is recognizable by a user, so that the user can recognize an accurate condition of the blood pressure pulse wave from which effect of respiratory variation and the like are removed.

Exemplary embodiments of the present invention the present invention provide a biological information measuring apparatus and a blood pressure analyzing method that, without complicating a configuration, can obtain a blood pressure condition in which effect of respiratory variation, body motion or the like is suppressed (cancelled).

What is claimed is:

1. A biological information measuring apparatus comprising:
   a blood pressure pulse wave measuring unit configured to measure a blood pressure pulse wave of a subject;
   a unit pulse wave producing unit configured to produce unit pulse waves from the blood pressure pulse wave based on an analysis of heart beats of the subject;
   a unit pulse wave extracting unit configured to calculate a blood pressure value of each of the unit pulse waves produced by the unit pulse wave producing unit, the blood pressure value being an average blood pressure value, a minimum pressure value or a maximum pressure value, to produce a histogram using the calculated blood pressure values, and to extract only unit pulse waves of a class including a mode value, an average value or a median value of the calculated blood pressure values; and
   an output unit configured to display at least one of: an average pulse wave, an average blood pressure value, and one or more of the unit pulse waves, based on the unit pulse waves extracted by the unit pulse wave extracting unit.

2. The biological information measuring apparatus according to claim 1, further comprising an electrocardiogram measuring unit configured to measure an electrocardiogram of the subject,
   wherein the unit pulse wave producing unit is configured to detect QRS waves in the electrocardiogram and to divide the blood pressure pulse waves by an RR interval to produce the unit pulse waves.

3. The biological information measuring apparatus according to claim 1, wherein the unit pulse wave extracting unit is configured to extract only the unit pulse waves of the class including the mode value.

4. The biological information measuring apparatus according to claim 1, wherein the output unit is configured to average the unit pulse waves extracted by the unit pulse wave extracting unit to calculate the average pulse wave, and to display the average pulse wave on a display screen.

5. The biological information measuring apparatus according to claim 1, wherein the output unit is configured to perform a statistical processing on the unit pulse waves extracted by the unit pulse wave extracting unit to calculate the average blood pressure value, and to display the average blood pressure value on a display screen.

6. The biological information measuring apparatus according to claim 1, wherein the output unit is configured to display the unit pulse waves on a display screen, wherein the unit pulse waves extracted by the unit pulse wave extracting unit and unit pulse waves not extracted by the unit pulse wave extracting unit are displayed with different display effects in a superposed manner.

7. The biological information measuring apparatus according to claim 1, wherein the unit pulse wave extracting unit is configured to extract only the unit pulse waves of the class including the mode value of the average blood pressure values.

8. A blood pressure analyzing method comprising:
   measuring a blood pressure pulse wave of a subject;
   producing unit pulse waves from the blood pressure pulse wave based on an analysis of heart beats of the subject;
   calculating a blood pressure value of each of the produced unit pulse waves, the blood pressure value being an average blood pressure value, a minimum pressure value or a maximum pressure value;
   producing a histogram using the calculated blood pressure values;
   extracting only unit pulse waves of a class including a mode value, an average value or a median value of the calculated blood pressure values; and
   displaying at least one of: an average pulse wave, an average blood pressure value, and one or more of the unit pulse waves,
   based on the extracted unit pulse waves.

9. A non-transitory computer readable medium storing a program that, when executed by a computer, causes the computer to execute a method comprising:
   producing unit pulse waves from a blood pressure pulse wave of a subject;
   calculating a blood pressure value of each of the produced unit pulse waves, the blood pressure value being an average blood pressure value, a minimum pressure value or a maximum pressure value;
   producing a histogram using the calculated blood pressure values;
   extracting only unit pulse waves of a class including a mode value, an average value or a median value of the calculated blood pressure values; and
   displaying at least one of: an average pulse wave, an average blood pressure value, and one or more of the unit pulse waves, based on the extracted unit pulse waves.

* * * * *